April 26, 1949. R. A. HARRIS Plant Pat. 833
PECAN TREE
Filed July 24, 1947
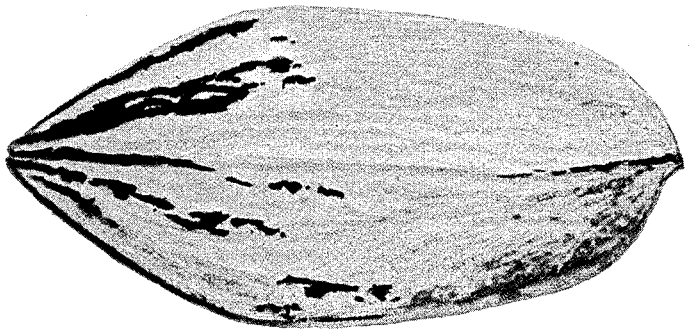
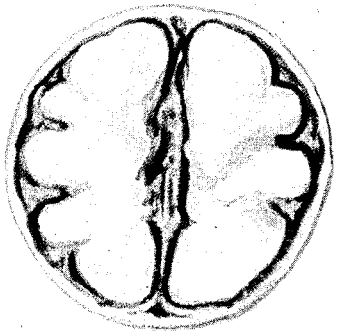
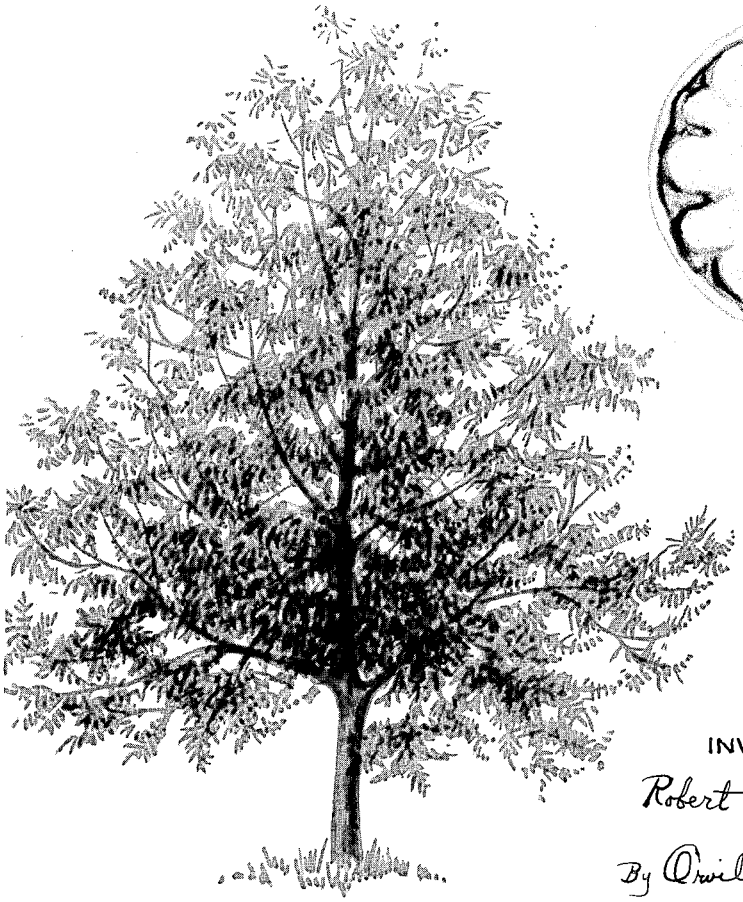
INVENTOR
Robert A. Harris
By Orville M. Kile
PLANT PATENT AGENT Patented Apr. 26, 1949

Plant Pat. 833

UNITED STATES PATENT OFFICE

833

PECAN TREE

Robert A. Harris, Arlington, Calif., assignor to
Lawrence Sherwood, Fullerton, Calif.

Application July 24, 1947, Serial No. 763,419
1 Claim. (Cl. 47—62)

My present invention relates to improvements in edible commercial pecans, particularly those known as dessert nuts which to be highly desirable must have pleasing texture and flavor, smooth fair-sized kernels, and a dense but thin shell which seals well to preserve the qualities of the kernel for a long period. Such nut should also have favorable shape for cracking and releasing the kernel whole or in unbroken halves, and should present a pleasing appearance.

My new variety produces a nut with all these qualities, with the added qualities of a tree which is symmetrical, has limbs which do not split or break easily, comes into early production, bears a consistently heavy crop, matures its crop early in the season and without splitting the shells, and has a wide climatic and soil range. I know of no other dessert nut commercially grown which is as high grade which comes into production so young and matures its crop as early in the season. Select (Plant Patent No. 510) comes into production the youngest of any variety known to me but it is of the general purpose type and not specifically the dessert nut type.

My new variety originated in a block of about 10,000 Schley seedlings grown from Schley nuts which were subject to open fertilization from surrounding varieties, mostly Schley. Therefore the pistillate parent is known to be Schley but the staminate parent is unknown. Out of these seedlings 36 were selected which by further selection were reduced at the end of the fifth season to four, of which my present new variety is one.

When asexually reproduced by budding, this new variety's characteristics appear to be permanent. Its good features were evident to me for several years before the original seedling bore nuts with which to be compared.

Accompanying illustrations show a side view and cross-section view of the nut of my new variety in natural colors. Also shown in the lower left-hand corner is a small sketch indicating the form of the tree.

Following is a detailed description of the tree and nuts of this new variety of pecan. Ordinary dictionary meanings are intended for the color terminology except where plate references are given, the latter indicating Ridgway's Color Standards and Nomenclature.

*The tree*

Growth: Vigorous; sturdy, with no breakage or splitting ever having been observed even where other varieties were badly damaged.

Form: Medium-spreading, upright form. Unusually well balanced, with limbs evenly and symmetrically placed around the trunk, mostly jutting out almost at right angles to the trunk and thus providing no decided V-forks to split.

Adaptability: Adapted to a wide climatic and soil range, exceeded in these respects by no other pecan variety known to me except my variety Select which is the subject of Plant Patent No. 510.

Productivity: The tree matures and begins to bear more quickly than any other pecan variety known to me except Select. It usually produces a few nuts the fourth year from planting a nursery tree, and gets into good production by the seventh year, when it has produced about 35 pounds. And in addition it bears a consistently heavy crop each year, the amount and consistency of which exceeds its parent Schley and most other varieties.

Disease resistance: Some varieties suffer from Rosette if there is not an abundance of zinc in the soil. Although all pecan trees require some zinc, I have never seen any of my new variety show any distress of this kind even where zinc had not been applied to the soil.

Trunk: Central trunk is very straight and the limbs symmetrically placed around it. Covered with rough bark at early age.

Lenticels: Many red colored lenticels are found on year-old wood.

Fruiting twigs: Many, indicating high production.

Foliage: Dense, the many leaves giving a large area of leaf surface. Leaves are medium in size, smooth and darker green than those of most pecan varieties. Leaves are joined to the small limbs and twigs by medium-sized midribs.

Blossoms: Catkins come in clusters of 6 or 8 and are about ¼ inch thick by 4¼ inches long. Pollen is rich yellow, of small grains which are easily carried by moderate air flow. Staminate bloom begins about April 15th and disseminates May 5 to 15. Pistillate bloom starts about May 1st and is receptive May 5 to 15.

*The nut*

Quantity: More abundant than any other as high grade dessert pecan variety known to me or of most other types of pecan. Produces about 35 pounds the seventh year from planting, and increases rapidly. Four-year-old trees I topped with single bud produced 55 pounds the fourth year.

Clusters: Average cluster contains about 5 nuts. They are not crowded together although the nut stems are short. The short stems prevent the nuts from being blown from the tree before maturity but permit them to harvest freely at maturity.

Maturity dates: Crop matures October 12 to 25 in elevations of 1500 to 1800 feet. Where observed at San Jacinto at an elevation of 1700 feet, the nuts matured October 10 to 15. Most varieties of pecans do not mature there before November 10 to 25 and frost and freezing weather often obtains by November first at this location. No other high grade dessert nut matures as early.

Tenacity to limbs: Very good. About the same as Schley.

Size: Larger than Schley when grown under similar conditions. About 1¾ inches to 2¼ inches in length and slightly over 3 inches in circumference at the hump.

Weight: About 60 nuts are usually required to make a pound. This is slightly heavier than Schley, which under same conditions of growth requires 70 to 75 nuts to make a pound.

Shape: Smooth outline with well balanced ends. Long and slender, with sharp apex and hump near apex end.

Color: Light tan with reddish-brown markings, principally at apex end.

Shell: Dense but thin and well sealed. Has no weakness of the divisional membrane. Does not split in process of maturing or later. Cracks and releases kernel easily—a little more readily than Schley when grown under similar circumstances. Keeps kernel well without allowing it to become rancid, as evidenced by the fact that I have kept some specimens perfectly for more than a year at ordinary room temperatures.

Husk: Above medium in thickness, with medium-sized ribs.

Kernel:

*Flavor.*—It is very difficult to describe the flavor, which is smooth and somewhat oily, very pleasing, and similar to that of Schley.

*Texture.*—Firm and crisp, fine grained and smooth. Compared with Schley, it is slightly more dense and therefore more resistant and crisp.

*Size.*—Medium. Fills shell exceptionally well.

Having thus disclosed my invention, I claim:

The new and distinct variety of pecan tree, substantially as herein shown and described, characterized particularly by the rapidity with which it comes into production; its consistently heavy crops; its early maturing season; its symmetrical form; its lack of breakage and splitting; its wide climatic and soil range; its medium-sized nuts having smooth outline, good balance, thin non-splitting shells well-sealed to preserve the kernel from rancidity for a long period, and plump kernel with pleasant flavor and crisp smooth texture.

ROBERT A. HARRIS.

No references cited.